United States Patent [19]

Kunkle, Jr.

[11] 4,012,471
[45] Mar. 15, 1977

[54] DISPOSABLE CONTAINER

[76] Inventor: George E. Kunkle, Jr., 4947 N. 113th, Omaha, Nebr. 68164

[22] Filed: June 6, 1975

[21] Appl. No.: 584,578

[52] U.S. Cl. .............................. 261/124; 128/187; 128/194; 206/438; 222/3; 222/180; 261/DIG. 65

[51] Int. Cl.² ...................................... A61M 15/00

[58] Field of Search ........ 261/122 R, 124, DIG. 65; 285/DIG. 2, DIG. 22; 222/180, 190, 3; 229/48 T; 206/205, 438, 484, 806; 128/192–194, 185–187; 215/304, 309, 259, 272

[56] References Cited

UNITED STATES PATENTS

| | | |
|---|---|---|
| 3,208,639 | 9/1965 | Marwell et al. ............ 261/DIG. 65 |
| 3,512,806 | 5/1970 | Romney et al. .................... 215/309 |
| 3,554,256 | 1/1971 | Anderson ........................... 128/272 |
| 3,682,168 | 8/1972 | Deaton ............................... 128/194 |
| 3,744,771 | 7/1973 | Deaton ............................... 261/122 |
| 3,807,713 | 4/1974 | Cornett et al. .................... 261/122 |
| 3,913,734 | 10/1975 | Siegel ............................... 206/484 |

Primary Examiner—Tim R. Miles
Assistant Examiner—Gregory N. Clements
Attorney, Agent, or Firm—Howard E. Moore; Gerald G. Crutsinger

[57] ABSTRACT

A disposable container wherein a thermoplastic sheet, having formed ribbed protrusions extending from one face of the sheet, forms one wall of the container. The protrusions are shaped to snap into a grooved coupling member such that the protrusions are urged into sealing relation with a gasket in the coupling member to detachably secure the container to the coupling member. At least one passage is formed in the thermoplastic sheet permitting delivery of fluid into or out of the container through the coupling member.

7 Claims, 11 Drawing Figures

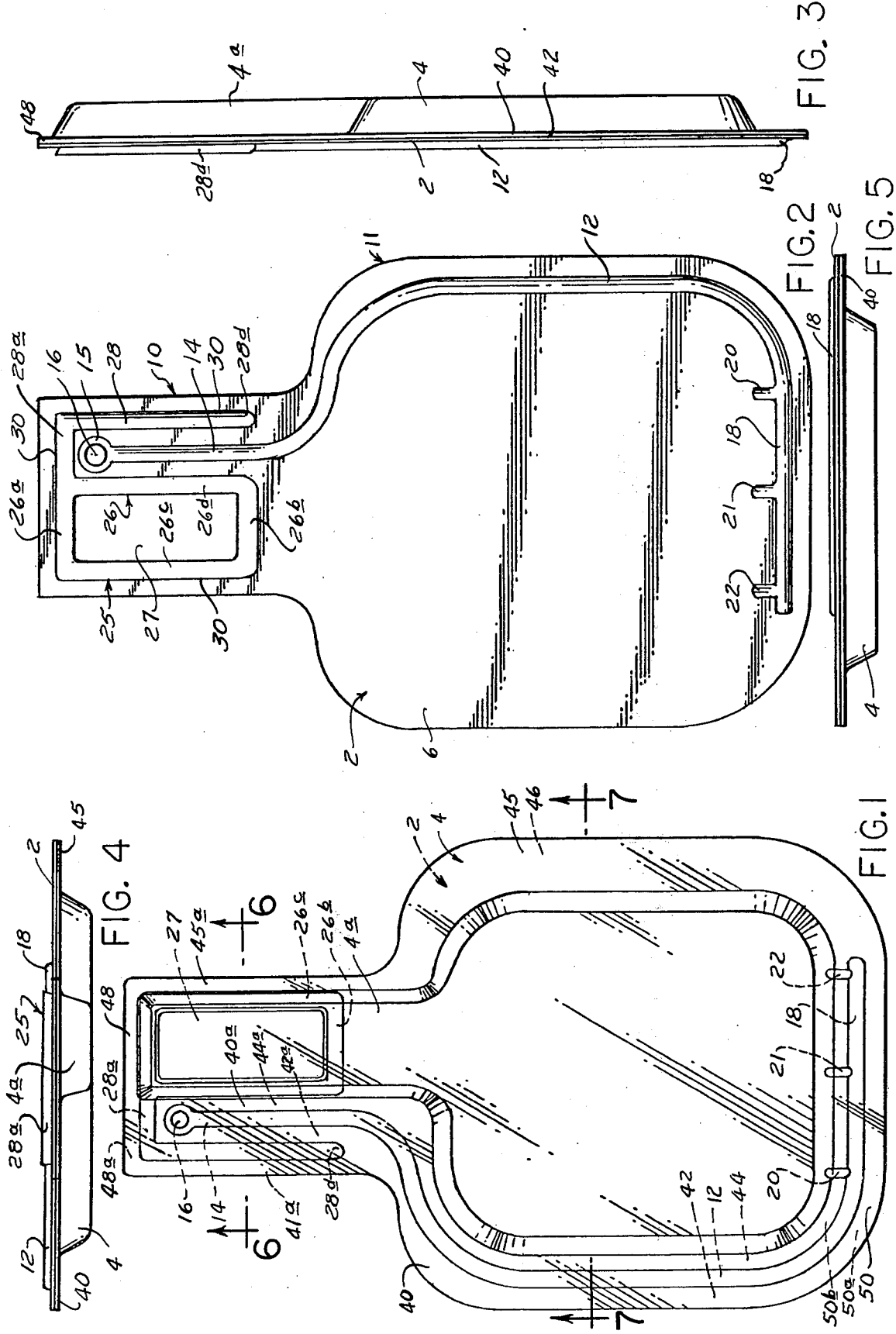

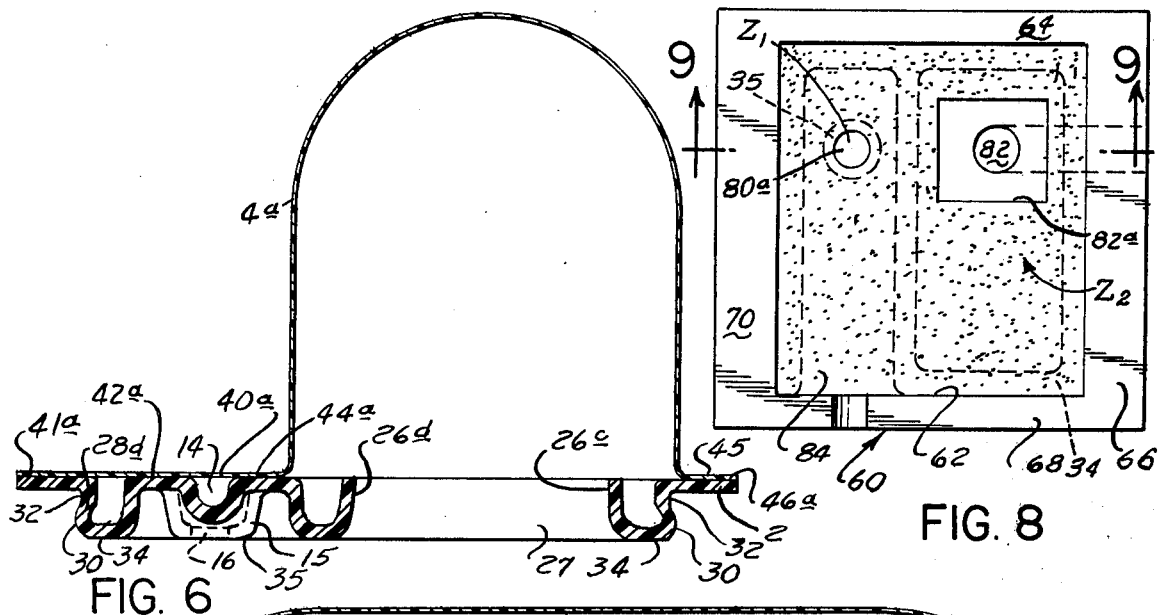
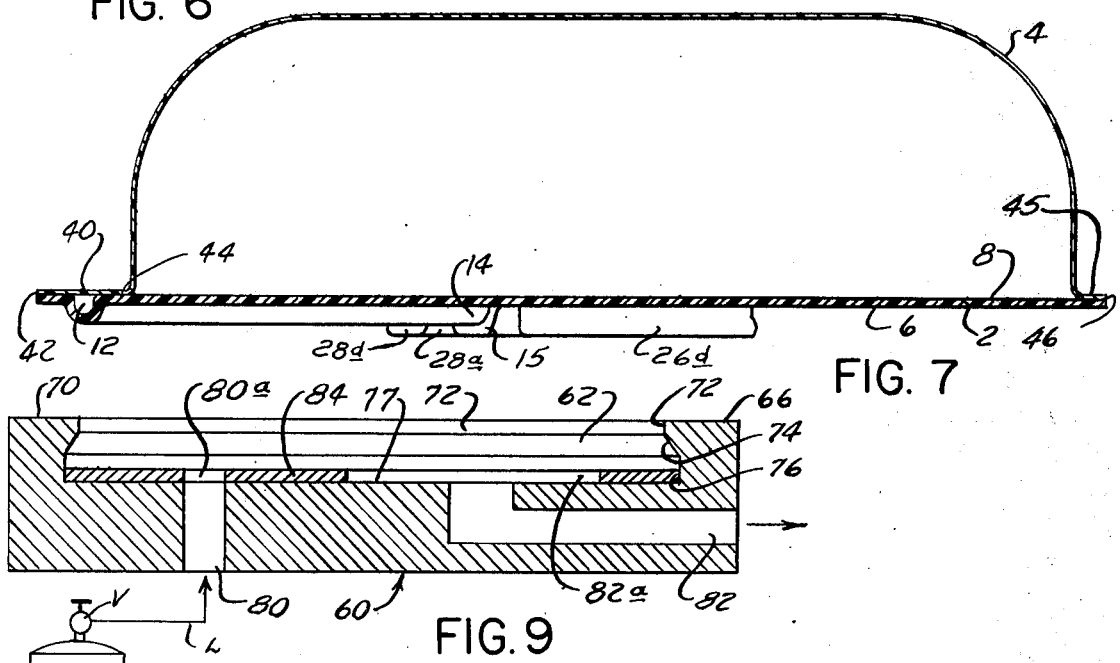
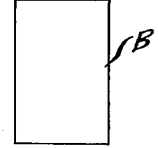
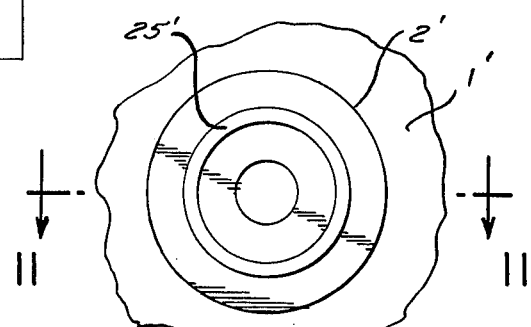
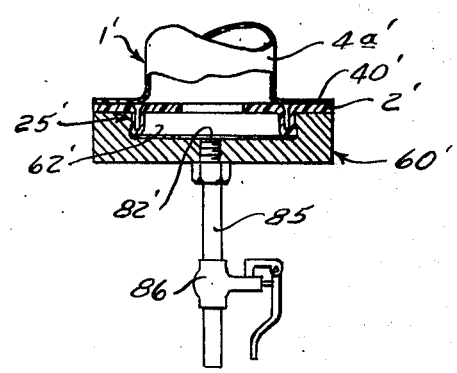

DISPOSABLE CONTAINER

BACKGROUND

Disposable containers constructed of various materials have been devised hereinbefore having an inlet or an outlet connectable by various coupling devices to dispensing machines and the like.

For example, when dispensing oxygen to a patient in a hospital, the oxygen gas is generally deficient in moisture unless some special means for increasing the moisture content is provided. Heretofore, water bags have been devised to permit delivery of oxygen to the interior of the bag below the surface of the water such that water is absorbed by oxygen flowing upwardly through the water. The water bag was generally connected by clamps, screws and the like to dispensing apparatus through which the oxygen was delivered to the patient.

In view of the necessity that sanitary conditions be maintained and that performance of the apparatus was highly reliable, connecting the water bag to the oxygen dispensing apparatus has proven to be a cumbersome and time consuming operation. Water bags for use in combination with oxygen dispensing apparatus are, in view of the required reliability of the apparatus, expensive.

Disposable containers, for example, plastic bags of milk for use in dispensing milk in cafeterias have been unduly complicated and expensive to manufacture.

SUMMARY OF INVENTION

I have devised an improved container construction wherein a sheet of thermoplastic material has a ribbed protrusion extending about the periphery of an inlet passage. The protrusions are shaped to snap into a grooved coupling member such that the protrusions are urged into sealing relation with a gasket in the coupling member.

In the first embodiment, the container comprises a nebulizer bag wherein the thermoplastic sheet has an inlet passage formed therein communicating with a channel extending downwardly to the bottom of the bag, the lower end of the channel communicating with the interior of the bag to permit delivery of fluid into the bag adjacent the lower end thereof. An outlet passage is formed adjacent the upper end of the bag through which fluid flows from the bag. The thermoplastic sheet is of substantially planar construction, portions of the sheet being deformed to form convex ribbed protrusions extending from one face of the sheet and concave channels in the other side of the sheet. Another wall of the container is preferably secured, as by heat sealing to the thermoplastic sheet adjacent the periphery of the first and second walls.

The second embodiment comprises a disposable container wherein a thermoplastic sheet is positioned across a hollow neck communicating with the interior of the container, the thermoplastic sheet having ribbed protrusions shaped to snap into a grooved coupling on a milk dispenser.

A primary object of the invention is to provide a disposable container, one wall of the container comprising a sheet having ribbed protrusions formed thereon shaped to snap into a grooved coupling member to detachably secure the container to the coupling member.

Another object of the invention is to provide a disposable container, particularly adapted for use as a nebulizer bag associated with oxygen dispensing apparatus wherein one wall of the container comprises a substantially planar vertically disposed sheet having ribbed protrusions formed on one face thereof to support the weight of the nebulizer bag and the contents thereof and a second wall of the bag being secured to the first wall wherein the second wall bridges a channel formed in the first wall to permit deliverying oxygen downwardly through the channel and releasing the oxygen adjacent the bottom of the nebulizer bag.

A further object of the invention is to provide a disposable container having formed ribbed protrusions formed thereon, edges of the protrusions forming a rib which is deformable to snap into a groove formed in a coupling member.

Other and further objects of the invention will become apparent upon referring to the detailed description hereinafter following and to the drawings annexed hereto.

DESCRIPTION OF DRAWING

Drawings of two embodiments of the invention are annexed hereto, so that the invention may be better and more fully understood, in which:

FIG. 1 is front elevational view of the disposable container;

FIG. 2 is a rear elevational view thereof;

FIG. 3 is a side elevational view thereof;

FIG. 4 is a top plan view thereof;

FIG. 5 is a botton view thereof;

FIG. 6 is a cross-sectional view taken along line 6—6 of FIG. 1;

FIG. 7 is a cross-sectional view taken along line 7—7 of FIG. 1;

FIG. 8 is an elevational view of a coupling member to which the container is detachably connectable;

FIG. 9 is a cross-sectional view taken along line 9—9 of FIG. 8;

FIG. 10 is an elevational view of a second embodiment of the apparatus; and

FIG. 11 is a cross-sectional view taken along line 11—11 of FIG. 10 having a coupling member associated therewith.

Numeral references are employed to designate like parts throughout the various figures of the drawing.

DESCRIPTION OF A PREFERRED EMBODIMENT

Referring to FIGS. 1–7 of the drawing, the numeral 1 generally designates a container comprising a semi-rigid sheet 2 of thermoplastic material and a flexible sheet 4 of plastic film, the sheets 2 and 4 being secured together adjacent peripheral edges thereof.

The semi-rigid sheet 2 is preferably a thermoplastic material that will repeatedly soften when heated and harden when cooled, for example, polyethylene, vinyl or styrene polymers and copolymers.

As best illustrated in FIGS. 1, 2, 6 and 7, sheet 2 of thermoplastic material has a first or outer surface 6 and a second or inner surface 8 and the sheet 2 is of substantially planar configuration.

In the particular embodiment of the invention illustrated in FIGS. 1–7, sheet 2 has a neck portion 10 projecting from an enlarged body portion 11 of the sheet.

Sheet 2 is deformed to provide a channel 12 having a first leg 14 communicating with the interior of a hollow frustroconical shaped projection 15 formed on the neck portion 10 of sheet 2 about an inlet passage 16.

The lower end of channel 12 communicates with a leg 18 extending transversely across the enlarged body portion 11 of sheet 2. Leg portion 18 of channel 12 communicates with branch channels 20, 21 and 22 which are spaced apart along the length of leg 18.

As best illustrated in FIG. 7, the outer surface 6 of sheet 2 is deformed outwardly forming a convex outer surface while the inner surface 8 of sheet 2 is concave between opposite ends of channel 12.

The neck portion 10 of sheet 2 is further deformed or shaped to provide a formed ribbed protrusion 25 which is connectable to a grooved coupling structure 60, as will be hereinafter more fully explained.

Protrusion 25, as illustrated in FIG. 2 of the drawing, extends outwardly from the outer face 6 of sheet 2 to form a substantially rectangular shaped protrusion 26 extending about the periphery of a rectangular shaped outlet passage 27 formed in the neck portion 10 of sheet 2. The rectangular shaped protrusion 26 comprises horizontally disposed parallel sides 26a and 26b and sides 26c and 26d which are parallel to each other but perpendicular to sides 26a and 26b. An inverted L-shaped protrusion having legs 28a and 28d is positioned such that legs 26a and 28a are axially aligned and coextensive while legs 26d and 28d are spaced apart and parallel to each other as well as parallel to leg 14 of channel 12.

Portions or sides 26a, 26b, 26c, 28a and 28d of protrusion 25 have a rib 30 extending along edges thereof, as best illustrated in FIG. 6. Portions 26a, 26b, 26c, 28a and 28d of projection 25 are of substantially identical cross-section.

By way of explanation, and not limitation, the particular sheet 2 illustrated in FIG. 6 of the drawing is constructed of polyethylene and has a thickness of 0.030 inches. Seat surface 32 on the outer edge of protrusion 26c extends perpendicularly from the outer surface 6 of sheet 2 a distance of 0.040 inches to intersect an arcuate surface having a radius of 0.100 inches forming rib 30 which extends outwardly from seat surface 32 a distance of 0.020 inches. Surface 34 is substantially parallel to outer surface 6 of sheet 2, forming a sealing surface to be urged into engagement with sealing apparatus in a coupling member 60, as will be hereinafter more fully explained.

From the foregoing it should be readily apparent that arcuate surfaces on ribs 30 on portions 26c and 28d of protrusion 25 are spaced apart a distance greater than seat surfaces 32 thereon. It should further be apparent that neck portion 10 of sheet 2, even though constructed of a very thin thermoplastic material, is relatively stiff in view of corrugated reinforcing provided by protrusion 25 and channel 14.

Referring to FIGS. 6 and 7 it will be noted that, except for those portions of sheet 2 adjacent protrusion 25 and channel 12, sheet 2 is relatively flat or planar.

Sheet 4 comprises a thin plastic film having edges thereon bonded to the inner surface 8 of sheet 2 along the marginal edges of sheet 2. If sheet 2 is constructed of polyethylene, sheet 4 is preferably low density polyethylene to facilitate heat sealing or bonding edges of sheets 2 and 4 together. Solvent and pressure may be employed for bonding edges of the sheets or adhesive may be employed if it is deemed expedient to do so.

As best illustrated in FIG. 7 the edge of sheet 4 is shaped to form a flange 40 which is bonded to surfaces 42 and 44 immediately adjacent opposite sides of channel 12 such that flange 40 bridges across channel 12 and forms one wall thereof. The opposite side of sheet 4 is shaped to form a flange 45 which is bonded to surface 46 on the inner face 8 of sheet 2.

Referring to FIG. 6 of the drawing, sheet 4 has a neck portion 4a having flanges 40a and 45a bonded to surfaces 42a, 44a, and 46a. The edge of flange 40a extends outwardly and is bonded to surface 41a on neck portion 10 of sheet 2.

The outer extremity of neck portion 4a of sheet 4 has a flange 48 bonded to surface 48a on neck portion 10 of sheet 2 while the opposite end of sheet 4 has a flange 50 formed thereon bonded to surfaces 50a and 50b on sheet 2.

From the foregoing it should be readily apparent that flanged portions 40 and 40a on sheet 4 bridge channel 12 and leg 14 of channel 12, while flanged portion 50 bridges leg 18 of channel 12 such that fluid flowing through inlet passage 16 is directed along leg 14 into channel 12 and along leg 18 into space between sheets 2 and 4 through branch channels 20, 21, and 22. As best illustrated in FIG. 1, it should be noted that the flanged portion 50 of sheet 4 is bonded to surfaces 50a and 50b on sheet 2. However, flanged portion 50 terminates intermediate opposite ends of branch channels 20, 21, and 22 permitting free passage of fluid through leg 18 of channel 12 into the interior of container 1.

Sheets 2 and 4 are preferably shaped as described herein by a vacuum forming process.

A coupling member 60, adapted to receive protrusions 25 on the neck portion 10 of sheet 2, is illustrated in FIGS. 8 and 9 of the drawing.

Coupling member 60 in the illustrated embodiment comprises a rectangular parallelopiped having a rectangularly shaped recess 62 formed therein bounded by surfaces 64, 66, 68, and 70 which extend about the outer periphery of recess 62.

As best illustrated in FIG. 9, walls of recess 62 are tapered forming a groove in the peripheral wall of recess 62.

The tapered wall in recess 62 is shaped to form a surface 72 which is substantially perpendicular to surfaces 64–70. Surfaces 72 are intersected by inclined surfaces 74 which intersect surfaces 76 which extend about the bottom 77 of recess 62. It should be appreciated that surfaces 72, 74, and 76 are arranged to form a socket to receive protrusion 25 on container 1.

Connector member 60 has an inlet passage 80 and an outlet passage 82 formed therein, and a gasket 84 having apertures 80a and 82a formed therein is bonded to the bottom wall 77 of recess 62. The gasket 84 is positioned to divide the interior of coupling member 60 into a pair of flow zones when protrusion 25 is positioned in recess 62. Inlet passage 16 in sheet 2 communicates with a first zone Z1 and outlet passage 27 communicates with a second Z2 zone. Portions of projection 15 and protrusions 25 which are urged into sealing engagement with gasket 84 are shown in dashed outline in FIG. 8 of the drawing.

It should be noted that the first zone Z1 is bounded by surface 35 on the end of hollow frusto-conical shaped projection 15, and that the second zone Z2 is bounded by sides 26a, 26b, 26c and 26d of the rectangular shaped portion 26 of protrusion 25.

Comparing FIGS. 6 and 9, it should be noted that surfaces 72 extending about the periphery of recess 62 are spaced apart a distance substantially equal to the distance between seat surfaces 32 on sides 26c and 28d of ribbed protrusion 25 on sheet 2. Thus, arcuate surfaces on rib 30 on protrusion 25 are deflected inwardly to pass through the opening in coupling member 60 bounded by surfaces 72. After ribs 30 pass surfaces 72, the ribs 30 are urged outwardly into engagement with inclined surfaces 74. The sealing surfaces 34 on protrusion 25 are urged into sealing engagement with the surface of gasket 84 while surface 35 about inlet passage 16 is urged into sealing engagement with the surface of gasket 84 adjacent aperture 80a.

SECOND EMBODIMENT

A second embodiment of the invention is illustrated in FIGS. 10 and 11 of the drawing.

In the second embodiment of the invention a sheet 2' having a ribbed protrusion 25' is secured to outwardly extending annular flange 40' on the neck 4a' of a container 1'.

Container 1' may assume any desired configuration and is constructed of any suitable material, such as low density polyethylene to form a bag containing liquid such as milk.

Coupling member 60' has a circular recess 62' formed therein connectable to the circular ribbed protrusion 25' in the manner hereinbefore described.

Coupling member 60' has an outlet opening 82' communicating with a hose 85 connected to a dispensing valve 86.

Since container 1' is flexible, it is not necessary to vent the interior thereof for liquid to flow through the neck 4' into hose 85 and to be dispensed through valve 86.

OPERATION

The operation and function of the first embodiment of the apparatus hereinbefore described is as follows:

If the container illustrated in FIG. 1 of the drawing is to be used as a nebulizer bag for humidifying oxygen, the inlet passage 80 in a coupling apparatus 60 is connected to a pressurized source of oxygen.

As diagrammatically illustrated in FIG. 9, a suitable source of oxygen comprises an oxygen bottle B having a valve V mounted thereon, the valve being connected to a line L for deliverying oxygen to the inlet passage 80.

Before connecting container 1 to coupling member 60 water or liquid medication is deposited in container 1.

Ribbed protrusion 25 is then inserted into recess 62 in coupling member 60, urging surfaces 34 and 35 into sealing engagement with gasket 84.

The outlet passage 82 in coupling member 60 is connected through a line to a conventional oxygen tent, oxygen dispensing mask or the like.

When valve V is opened oxygen flows through passages 80 and 80a, and through inlet passage 16 into leg 14 of channel 12. Oxygen flows from leg 18 of channel 12 through branch channels 20, 21 and 22 into the interior of container 1 and then bubbles upwardly through liquid contained in container 1 while flowing to the outlet passage 27. It should be readily apparent that liquid is absorbed by the oxygen passing through the liquid.

The weight of container 1 is supported by the ribbed protrusion 25 which extends outwardly from the outer face 6 of sheet 2.

It should be readily apparent that container 1 is disengaged from coupling member 60 by grasping the enlarged body portion 11 of the container and pulling outwardly to disengage ribbed protrusion 25 from recess 62 in coupling member 60 and a new container 1 is connectable to coupling member 60 by positioning protrusion 25 adjacent recess 62 and applying an inward force snapping protrusion 25 into recess 62.

From the foregoing it should be readily apparent that the apparatus hereinbefore described accomplishes the objects of the invention. It should be appreciated that container 1 comprises two vacuum formed sheets of thermoplastic material which are bonded together about the peripheral edges thereof to provide a nebulizer bag of extremely simple construction which is connectable to a coupling member without requiring the use of clamps, screws and the like.

It should be appreciated that other and further embodiments of the invention may be devised without departing from the basic concept thereof.

Having described my invention, I claim:

1. A container connectable to a coupling member having a groove formed in a wall of a recess in the coupling member, the container comprising: a first sheet of stiff thermoplastic material forming a first wall of the container, said first sheet having an inlet passage and an outlet passage extending therethrough; a protrusion on said first sheet, said protrusion extending exteriorly of the container and around the periphery of the outlet passage and about the inlet passage; a rib on said protrusion, said protrusion and said rib being of integral construction and being deformable to disengageably secure the rib on the protrusion in the groove in the wall of the recess in the coupling member; sealing surfaces about said inlet passage and about said outlet passage, said rib when positioned in the recess in the coupling being adapted to urge each of said sealing surfaces into sealing relation with a surface on the coupling member; and a second sheet having flanges extending about the periphery thereof, said flanges being secured to said first sheet of stiff thermoplastic material such that said second sheet forms a second wall of the container.

2. The container of claim 1, said inlet passage being spaced from said outlet passage, and said protrusion being shaped to extend between said inlet passage and said outlet passage such that the recess in the coupling member is divided into a pair of zones, one of said zones communicating with said inlet passage and the other of said zones communicating with said outlet passage.

3. The container of claim 2, the first sheet of stiff thermoplastic material comprising: a substantially planar sheet deformed to provide a channel extending along a marginal edge of the sheet, one end of said channel communicating with said inlet passage and a second end of said channel terminating at a position spaced from said inlet passage; said flanges on said second sheet being bonded to said first sheet so as to bridge said channel intermediate opposite ends of said channel.

4. A container comprising: a first substantially flat sheet having a body portion and a neck portion, said neck portion having inlet and outlet passages extending therethrough, said neck portion of said first sheet being corrugated to form a hollow projection about said inlet passage and a protrusion about said outlet passage, said body portion of said first sheet being formed to provide a channel having a first leg communicating with the interior of the projection about the inlet passage and having a second leg terminating adjacent the lower end of the body portion of the first sheet; a second sheet of flexible material having flanges extending about the periphery thereof, said flanges being secured to said first sheet to bridge across portions of the first and second legs of said channel and being secured to encircle the neck and body portion of said first sheet, the lower end of said second leg of said channel communicating with space between said first and second sheets such that fluid flowing through said inlet passage is directed along said first and second legs into space between said first and second sheets; said protrusion on said neck portion of said first sheet detachably securing said first sheet to a system to deliver fluid to said inlet passage and to receive fluid flowing from said outlet passage.

5. The container of claim 4, said first sheet being further corrugated to form a rib on said protrusion such that said protrusion is configured to snap into a grooved coupling structure to form a pair of flow zones, one of said flow zones communicating with said inlet passage and the other of said flow zones communicating with said outlet passage.

6. The container of claim 5, said hollow projection about the inlet passage comprising a truncated conical shaped portion of the first sheet, the inlet passage being formed in said projection.

7. The container of claim 6, said outlet passage being rectangular shaped, and said protrusion having a rectangular shaped portion and having legs extending therefrom to form an inverted L-shaped portion on said protrusion, the rib on said protrusion being arranged to simultaneously urge surfaces on said truncated conical shaped projection about the inlet passage and surfaces on said rectangular shaped portion about said outlet passage into sealing relation with surfaces on a coupling member when the rib is snapped into a groove formed in the wall of a rectangular shaped recess in a coupling member.

* * * * *